United States Patent [19]
Brown et al.

[11] Patent Number: 5,246,104
[45] Date of Patent: * Sep. 21, 1993

[54] MOLDED SUTURE RETAINER

[75] Inventors: David L. Brown, Wallingford; Henry A. Holzwarth, Weston, both of Conn.

[73] Assignee: United States Surgical Corporation, Norwalk, Conn.

[*] Notice: The portion of the term of this patent subsequent to Oct. 13, 2009 has been disclaimed.

[21] Appl. No.: 637,465

[22] Filed: Jan. 4, 1991

Related U.S. Application Data

[63] Continuation-in-part of Ser. No. 388,152, Aug. 1, 1989, and a continuation-in-part of Ser. No. 566,263, Aug. 13, 1990, and a continuation-in-part of Ser. No. 568,089, Aug. 16, 1990.

[51] Int. Cl.$^5$ .............................................. A61B 17/06
[52] U.S. Cl. .................... 206/63.3; 206/471; 206/227
[58] Field of Search .............. 206/63.3, 227, 471, 206/469, 467, 461, 339

[56] References Cited

U.S. PATENT DOCUMENTS

| | | | |
|---|---|---|---|
| 3,256,981 | 6/1966 | Kurtz | 206/63.3 |
| 3,301,393 | 1/1967 | Regan, Jr. et al. | 206/63.3 |
| 3,338,401 | 8/1967 | Regan, Jr. | 206/63.3 |
| 3,490,192 | 1/1970 | Regan, Jr. | 53/432 X |
| 3,972,418 | 8/1976 | Schuler et al. | 206/63.3 |
| 4,192,420 | 3/1980 | Worrell, Sr. et al. | |
| 4,201,216 | 5/1980 | Mattei | |
| 4,204,542 | 5/1980 | Bokros et al. | |
| 4,206,101 | 6/1980 | Wysong | |
| 4,249,656 | 2/1981 | Cerwin et al. | |
| 4,253,563 | 3/1981 | Komarnycky | |
| 4,261,463 | 4/1981 | Shave | |
| 4,284,194 | 8/1981 | Flatau | |
| 4,321,038 | 3/1982 | Porteous | |
| 4,330,338 | 5/1982 | Banker | |
| 4,338,397 | 7/1982 | Gilbert et al. | |
| 4,362,162 | 12/1982 | Nakajima et al. | |
| 4,363,319 | 12/1982 | Altshuler | |
| 4,369,880 | 1/1983 | Giggey et al. | |
| 4,399,157 | 8/1983 | Caporaso | |
| 4,406,363 | 9/1983 | Aday | |
| 4,412,614 | 11/1983 | Ivanov et al. | |
| 4,412,617 | 11/1983 | Cerwin | |
| 4,412,986 | 11/1983 | Kawata et al. | |
| 4,418,691 | 12/1983 | Yannas et al. | |
| 4,424,898 | 1/1984 | Thyen et al. | |
| 4,427,109 | 1/1984 | Roshdy | |
| 4,432,964 | 2/1984 | Shell et al. | |
| 4,439,181 | 3/1984 | Blachshear et al. | |
| 4,444,927 | 4/1984 | Borysko | |
| 4,466,431 | 8/1984 | Tharrat et al. | |
| 4,469,837 | 9/1984 | Cattaneo | |
| 4,483,427 | 11/1984 | Cerwin et al. | |
| 4,491,218 | 1/1985 | Aday | |
| 4,496,045 | 1/1985 | Ferguson et al. | |
| 4,519,501 | 5/1985 | Cerwin | |
| 4,523,591 | 6/1985 | Kaplan et al. | |
| 4,528,186 | 7/1985 | Nishmura et al. | |
| 4,532,929 | 8/1985 | Mattei et al. | |
| 4,533,041 | 8/1985 | Aday et al. | |
| 4,546,769 | 10/1985 | Planck et al. | |

(List continued on next page.)

FOREIGN PATENT DOCUMENTS 3710177 12/1988 Fed. Rep. of Germany .
1475399 2/1967 France .

Primary Examiner—David T. Fidei
Assistant Examiner—Jacob K. Ackun, Jr.
Attorney, Agent, or Firm—Thomas R. Bremer; Peter G. Dilworth; Rocco S. Barrese

[57] ABSTRACT

A molded suture retainer is provided for retaining and storing sutures. Both absorbable and nonabsobable sutures fabricated from natural or synthetic materials can be advantageously retained and stored therein. The retainer is characterized by a wide spiraling oval passageway with minimal convolutions covered by a cover sheet. The length of the passageway is preferably proportional to ⅓ to ½ the overall length of the suture to be retained therein. Recesses are provided for receiving package stabilizing agents and/or needle parks. Sutures packaged in accordance with the invention exhibit fewer kinks and bends than prior packaged sutures.

33 Claims, 9 Drawing Sheets

U.S. PATENT DOCUMENTS

| | | |
|---|---|---|
| 4,549,649 | 10/1985 | Roshdy . |
| 4,555,016 | 11/1985 | Aday et al. . |
| 4,572,363 | 2/1986 | Alpern . |
| 4,574,957 | 3/1986 | Stead . |
| 4,579,731 | 4/1986 | Fox, Jr. et al. . |
| 4,588,400 | 5/1986 | Ring et al. . |
| 4,588,583 | 5/1986 | Pletsch et al. . |
| 4,594,240 | 6/1986 | Kawata . |
| 4,595,102 | 6/1986 | Cianci et al. . |
| 4,595,713 | 6/1986 | St. John . |
| 4,600,743 | 7/1986 | Shizuki et al. . |
| 4,603,538 | 8/1986 | Shave . |
| 4,615,435 | 10/1986 | Alpern et al. . |
| 4,620,974 | 11/1986 | Hersh et al. . |
| 4,621,052 | 11/1986 | Sugimoto . |
| 4,621,638 | 11/1986 | Silvestrini . |
| 4,624,256 | 11/1986 | Messier et al. . |
| 4,649,920 | 3/1987 | Rhum . |
| 4,653,497 | 3/1987 | Bezwada et al. . |
| 4,674,629 | 6/1987 | Gunselman . |
| 4,705,820 | 11/1987 | Wang et al. . |
| 4,708,241 | 11/1987 | Black . |
| 4,711,241 | 12/1987 | Lehmann . |
| 4,717,717 | 1/1988 | Finkenaur . |
| 4,742,003 | 5/1988 | Derynick et al. . |
| 4,743,679 | 5/1988 | Cohen et al. . |
| 4,792,336 | 12/1988 | Hlavacek et al. . |
| 4,801,456 | 1/1989 | Drengler . |
| 4,806,621 | 2/1989 | Kohn et al. . |
| 4,813,537 | 3/1989 | Okuhara et al. . |
| 4,861,757 | 8/1989 | Antoniades et al. . |
| 4,874,746 | 10/1989 | Antoniades et al. . |
| 4,906,474 | 3/1990 | Langer et al. . |
| 4,911,908 | 3/1990 | Estis et al. . |
| 4,913,903 | 4/1990 | Sudmann et al. . |
| 4,917,685 | 4/1990 | Viswanathan et al. . |
| 4,929,442 | 5/1990 | Powell . |
| 4,944,948 | 7/1990 | Uster et al. . |
| 4,961,498 | 10/1990 | Kakinski et al. . |
| 4,967,902 | 11/1990 | Sobel et al. . |
| 5,037,429 | 8/1991 | Hermes et al. . |
| 5,081,150 | 1/1992 | Reul et al. . |
| 5,154,283 | 10/1992 | Brown ............................ 206/471 X |

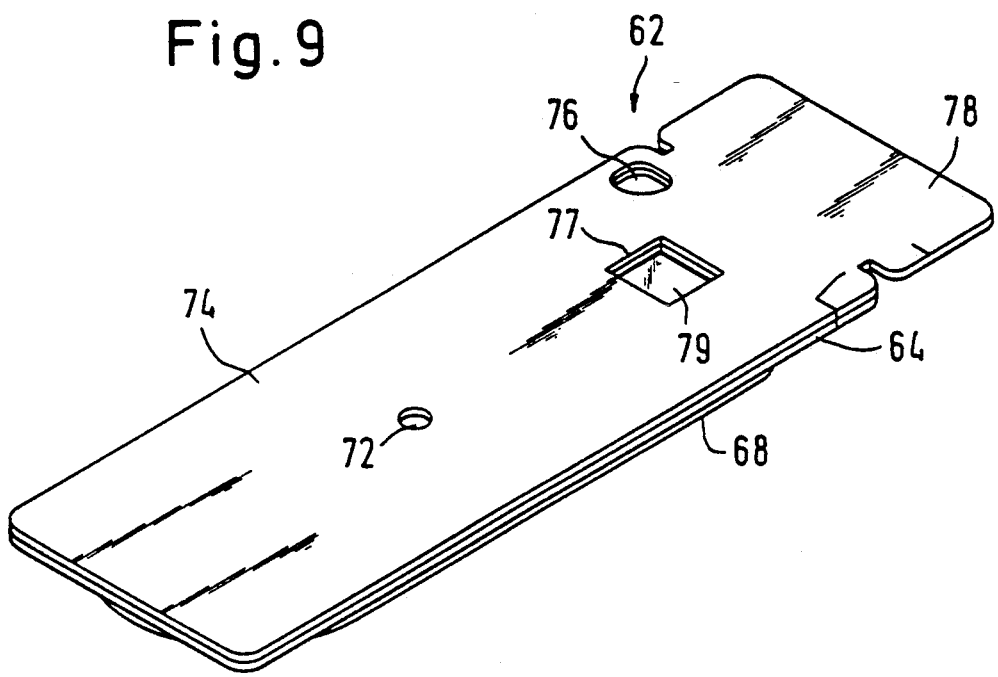
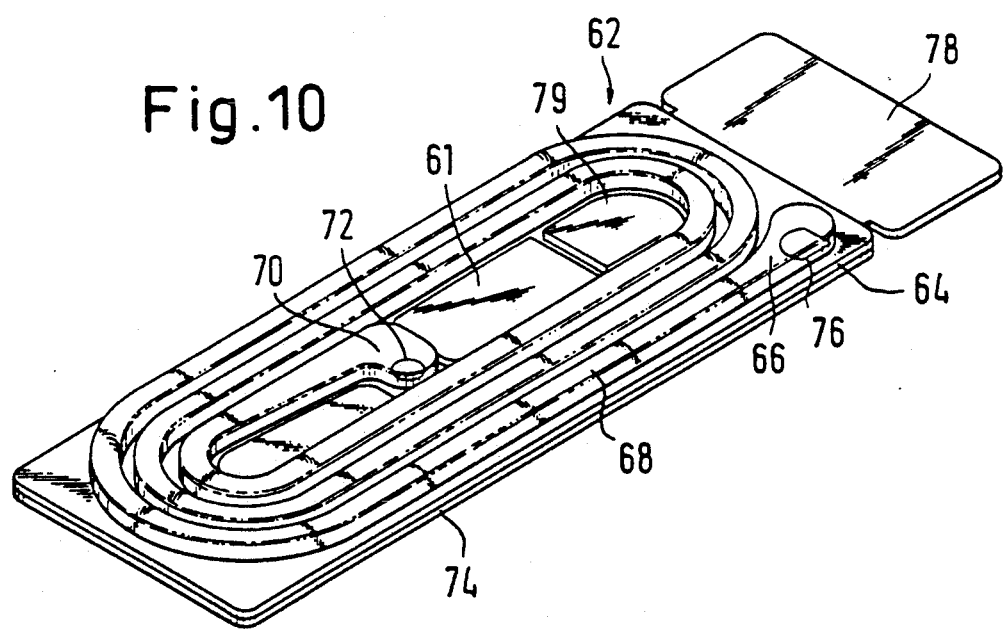

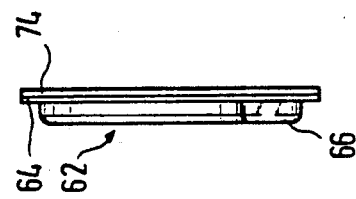
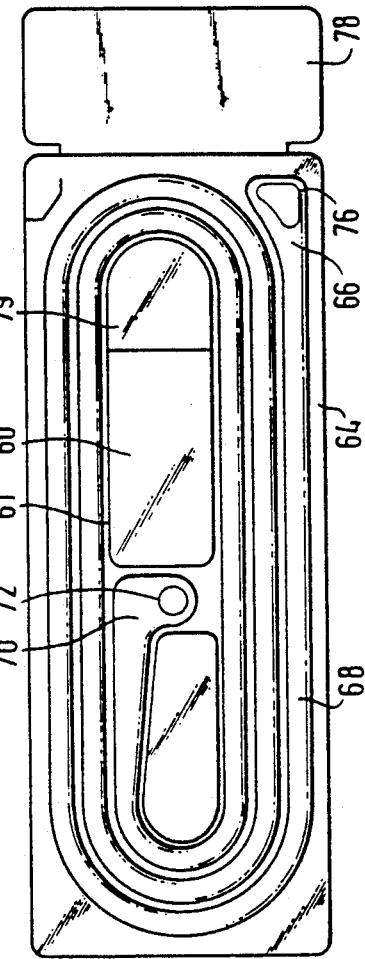
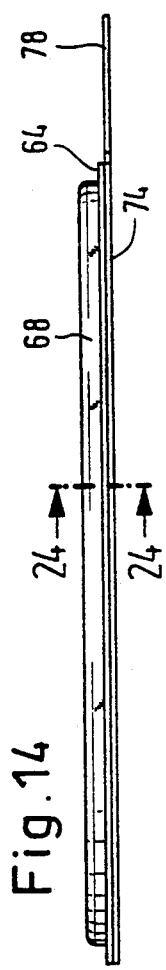
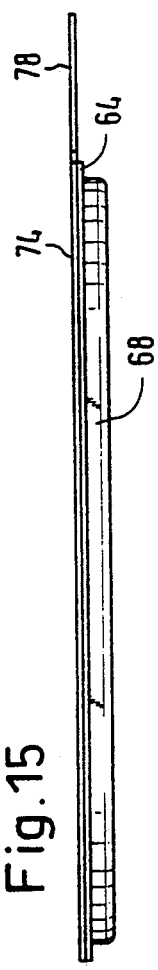
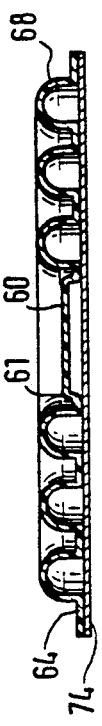
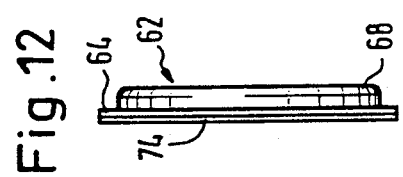

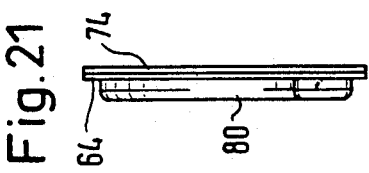
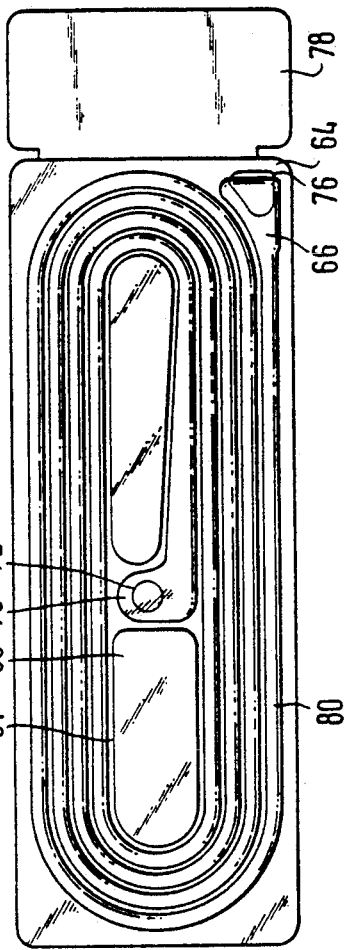
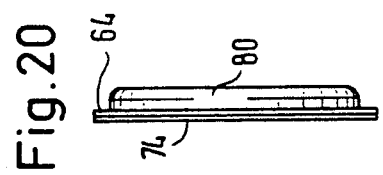
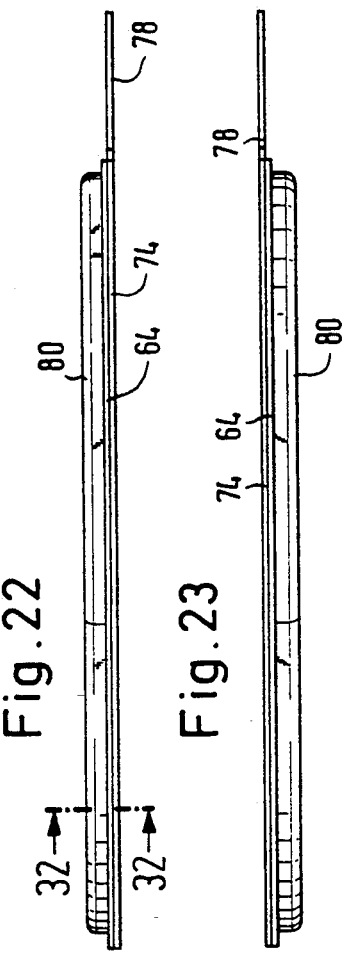
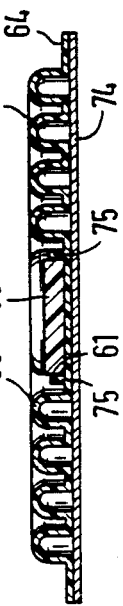

MOLDED SUTURE RETAINER

CROSS REFERENCE TO RELATED APPLICATIONS

This is a continuation-in-part of copending application Ser. Nos. 07/388,152 filed Aug. 1, 1989, Ser. No. 07/566,263 filed Aug. 13, 1990 and Ser. No. 07/568,089 filed Aug. 16, 1990, the entire specifications of which are incorporated herein by reference.

BACKGROUND OF THE INVENTION

1. Field of the Invention

The present invention relates to packaging of sutures and, more particularly, to improved packages for sutures to improve loading and handling characteristics thereof.

2. Description of the Related Art

This invention relates to molded suture retainers and their use for packaging sutures, including nonabsorbable and synthetic absorbable sutures, to improve the out of package flexibility and handling characteristics of the sutures after storage. Sutures can be either monofilament or braided and are available in a wide variety of materials including cotton, silk, stainless steel, catgut, and dacron, nylon or other synthetic materials.

Synthetic absorbable sutures are typically formed using polymers and copolymers of glycolic acid (i.e., hydroxyacetic acid), the cyclic dimer of glycolic acid ("glycolide"), lactic acid, the cyclic dimer of lactic acid ("lactide") and related monomers, polydioxanone, polytrimethylene carbonate, polyalkylene glycol, polycaprolactone, their copolymers, etc.

Many types of packages for sutures are known in the art including those described in U.S. Pat. Nos. 2,917,878; 2,949,181; 2,965,225; 3,043,067; 3,143,209; 3,147,861; 3,163,288; 3,202,272; 3,221,873; 3,256,981; 3,280,971; 3,315,802; 3,319,782; 3,338,401; 3,357,549; 3,490,192; 3,613,879; 3,627,120; 3,642,126; 3,648,949; 3,8766,068; 3,939,969; 4,014,433; 4,069,912; 4,089,410; 4,135,623; 4,168,000; 4,249,656; 4,261,463; 4,284,194; 4,369,880; and, 4,549,649.

Nonabsorbable sutures may be packaged and/or sterilized using conventional techniques without concern for degradation of the suture material through hydrolysis. Synthetic absorbable sutures, in contrast, typically are packaged in moisture impervious foil laminate envelopes wherein the suture is wound in a FIG. 8 pattern on a paper retainer. Typical retainers of this type are shown in U.S. Pat. Nos. 4,131,195, 4,192,420, 4,249,656, 4,253,563 and 4,063,638.

Molded suture packages having narrow convoluted passageways configured to predetermine the coil of the suture are also known. For example, U.S. Pat. Nos. 3,338,401 and 3,490,192 disclose molded suture packages wherein one or more elongated sutures are retained in a coiled narrow passageway having a plurality of convolutions therein. These passageways are proportioned to accommodate an entire length of the suture end to end without folding. These passageways are typically molded into a plastic carrier material and define a small diameter hollow plastic tube. The patents also discuss the loading of sutures into the passageways using a vacuum. Molded retainers have been used to package some nonabsorbable sutures, but have not been adopted for widespread use in packaging sutures, particularly synthetic absorbable sutures.

Typical commercially available synthetic absorbable sutures are packaged under extremely dry conditions, and are relatively stiff and inflexible upon removal from the packaging. Such sutures exhibit "memory" which causes the suture to retain or resume the customary FIG. 8 or coiled shape assumed by sutures packaged in such a configuration in a cardboard or paper retainer. This effect is undesirable since the suture must be straightened prior to use. The figure 8 configuration has also been found to introduce undesirable kinks and binds in the suture. It is believed that the extremely dry conditions required for packaging prior synthetic absorbable sutures, together with the suture memory effect created by such packaging and the number and radius of curvature of the convolutions required to accommodate full length sutures may combine to make it difficult or impossible to withdraw the suture from such packaging without breaking the suture or detaching the needle from an armed suture. This is particularly believed to be true in the case of sutures having lengths in excess of 20 inches wherein the passageways must be compressed and convoluted in order to accommodate the suture end to end.

Therefore, it would be highly desirable to provide a molded suture retainer and method of loading same which permits the suture to be stored more efficiently without the introduction of kinks and bends.

Accordingly, it is one object of the invention to provide a molded suture retainer which permits easy installation, storage and removal of sutures without kinks and bends therein.

It is a further object of the present invention to provide a molded suture retainer and method of loading same which provides more efficient loading, storage and removal of long length sutures.

It is another object of the present invention to provide a molded suture retainer for efficiently storing surgical sutures fabricated from hydrolytically unstable polymers.

These and other highly desirable and unusual results are accomplished by the present invention in a molded suture retainer which permits the loading and efficient storage of sutures and easy removal without kinks and bends.

Objects and advantages of the invention are set forth in part herein and in part will be obvious herefrom, or may be learned by practice with the invention, which is realized and attained by means of the instrumentalities and combinations pointed out in the appended claims.

The invention consists of the novel parts, constructions, arrangements, combinations, steps and improvements herein shown and described.

SUMMARY OF THE INVENTION

According to the present invention, a molded suture retainer is provided for retaining and storing sutures constructed of natural or synthetic materials including both absorbable and nonabsorbable sutures. In some embodiments, the retainer comprises a molded member defining a wide passageway open at the top and sufficient for holding a plurality of strands of sutures therein. These passageways are formed in an oval configuration spiraling toward the interior of the retainer with a minimum number of convolutions. For long sutures the length of the passageway is preferably proportional to $\frac{1}{3}$ to $\frac{1}{2}$ the overall length of the suture to be retained therein. Other proportions are also contemplated.

One end of the passageway serves as a suture receiving section to facilitate loading of the sutures. A vacuum receiving section is placed at the opposite end of the passageway to allow a vacuum to be drawn through the passageway to help position the sutures therein. This vacuum receiving section is preferably formed in an angular configuration with the vacuum hole offset from the end of the passageway to facilitate loading without the risk of drawing the suture end out of the hole.

The present invention contemplates the loading and storage of both armed sutures, i.e. sutures having needles attached thereto, and unarmed sutures without needles attached.

The molded suture retainer is further provided with a recessed compartment for containing a package stabilizing element and, where desired, a molded needle park for safely and securely retaining the needles of retained armed sutures. The term "package stabilizing element" as used herein refers to a material which maintains a stabilizing agent solvent level within a sealed package against any substantial increase or decrease, and specifically includes but is not limited to a mass of stabilizing agent within the package separate and apart from the retained suture. The term "stabilizing agent" as used herein refers to a material which, when associated with a polymeric article susceptible to hydrolysis, improves the storage stability of the polymeric article and eliminates any need to store the article in an artificially-maintained very dry environment. In the context of the preferred embodiment of the invention, water is the stabilizing agent solvent and the package stabilizing element will hereinafter be discussed in the context of water based systems, but should not be construed to be limited thereto.

The stabilizing element and/or needle park compartments are preferably recessed within the confines of the spiral passageway and do not extend in height beyond the dimensions of the molded suture retainer. This configuration facilitates easy and efficient stacking of multiple retainers.

A cover sheet is used to overlie the open top of the retainer. The cover sheet has a vacuum aperture and suture entrance aperture formed therein. The vacuum aperture aligns and communicates with the vacuum receiving section of the passageway while the suture entrance aperture aligns and communicates with the suture receiving section of the passageway. Where desired, special needle holding sections or a foam needle park can be added to the retainer for convenient needle positioning. The cover sheet may also include a fold over section to cover the needle when packaged, but which is moved to an open position upon opening the outer pouch in order to reveal the needle.

The retainer, when loaded with synthetic absorbable suture material, is preferably placed into an open foil laminate envelope where it is subject to treatment in an ethylene oxide gas sterilization cycle. The sterile retainer and its contents are then equilibrated, such as in a dew point controlled environment, until a desired moisture level is attained, and sealed.

When loaded with nonabsorbable sutures the retainer may be sealed in a "breather pouch", i.e. a two layer package consisting of a porous fibrous layer sealed to a plastic sheet material and sterilized.

In one embodiment of this invention, the suture is advantageously folded prior to positioning within the passageway. For double armed or long length sutures, the suture preferably is folded either in half or in thirds. Where exceptionally long sutures are contemplated, folding can be in fourths or fifths or close approximations thereof.

For an armed suture, loading is accomplished by feeding the end opposite the needle into the suture entrance aperture. A vacuum is drawn on the passageway adjacent the vacuum aperture and serves to draw the suture, which may be folded, into the passageway.

BRIEF DESCRIPTION OF THE DRAWINGS

The accompanying drawings, referred to herein and constituting a part hereof, illustrate the preferred embodiments of the molded suture retainer of the present invention, and together with the description serve to explain the principles of the invention.

FIG. 9 is a perspective view of the top of a molded suture retainer in accordance with another embodiment of the present invention.

FIG. 10 is perspective view of the bottom of a molded suture retainer in accordance with the embodiment of FIG. 9.

FIG. 11 is a bottom plan view of the molded suture retainer of FIG. 9.

FIGS. 12 and 13 are end views of the molded suture retainer of FIG. 9.

FIGS. 14 and 15 are side views of the molded suture retainer of FIG. 9.

FIG. 16 is an end view in cross section taken along line 16—16 of FIG. 14.

FIG. 19 is a bottom view of the molded suture retainer of FIG. 17.

FIGS. 20 and 21 are end views of the molded suture retainer of FIG. 17.

FIGS. 22 and 23 are side views of the molded suture retainer of FIG. 17.

FIG. 24 is an end view in cross section taken along lines 24—24 of FIG. 22.

DETAILED DESCRIPTION OF THE PREFERRED EMBODIMENTS

Figure 1A:
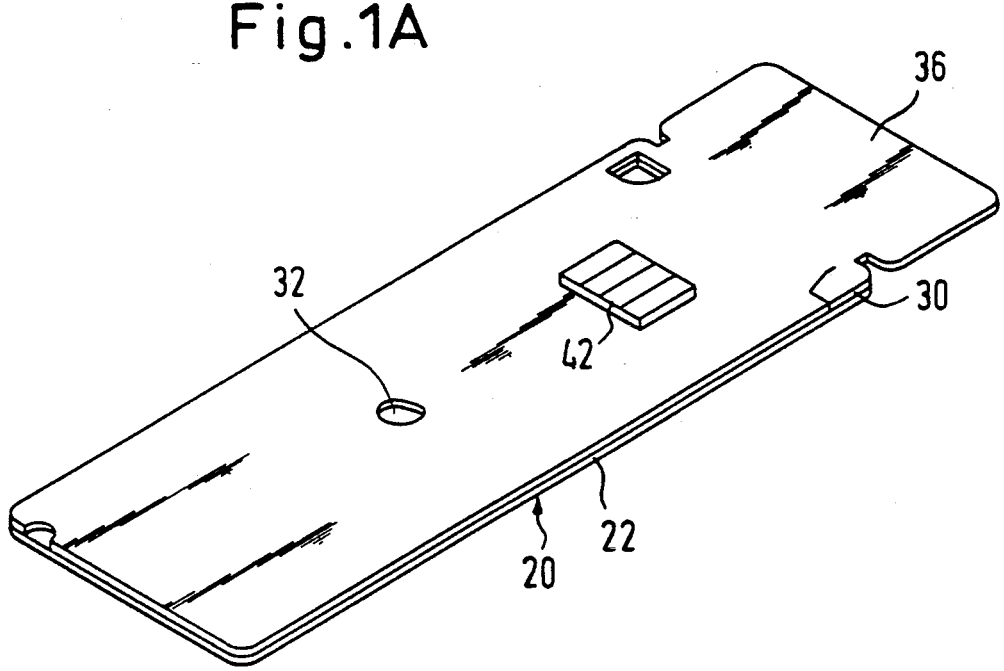
FIGS. 1A and 1B are perspective views of a preferred embodiment of a molded suture retainer in accordance with the present invention.
Figure 1B:
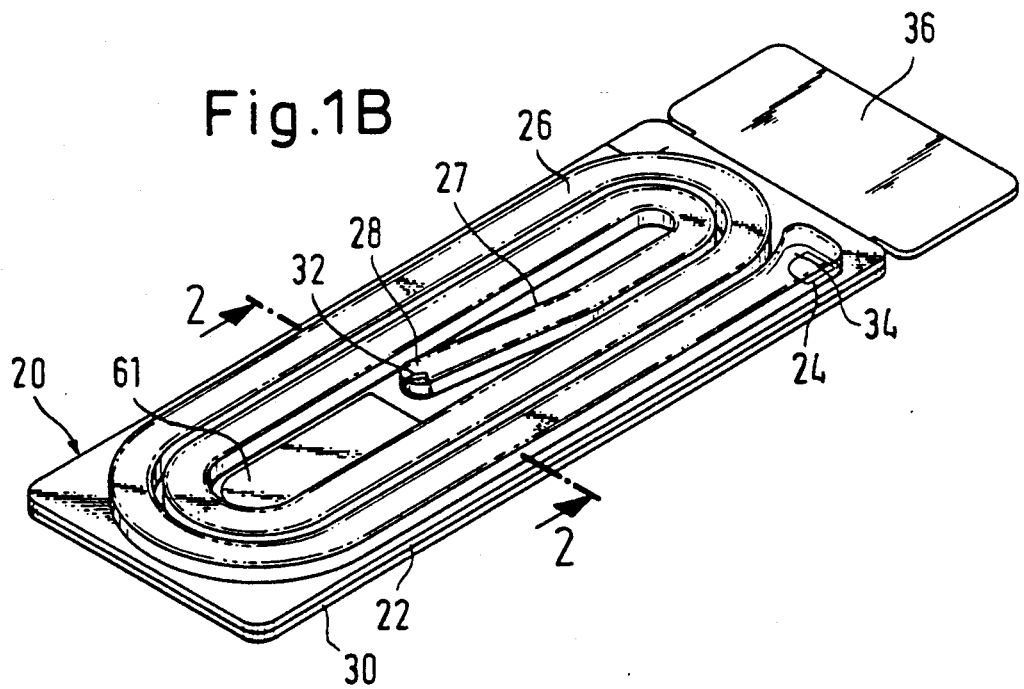

Referring now to FIGS. 1A and 1B, there is shown perspective views of a molded suture retainer 20 in accordance with the invention. The molded suture retainer illustrated in FIGS. 1A and 1B finds particular application for holding double or triple folded sutures of up to or more than 36 inches in length. Preferably, the molded suture retainer is made from a moldable transparent plastic material such as, for example, polyethylene terapthalate (PETG), Eastman Kodak 6763.

As shown, retainer 20 has a base 22 and an enlarged suture receiving section 24 leading to a relatively wide passageway 26 having minimal convolutions. The passageway 26 follows an oval pattern spiraling toward the approximate center through four turns to a terminus section 27 formed at a slight angle to the longitudinal axis of retainer 20 and terminates at a central vacuum receiving section 28.

Figure 2:
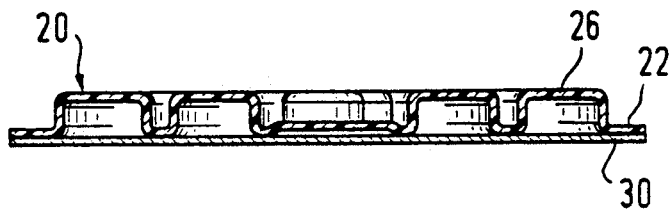
FIG. 2 is a cross-sectional view of the retainer of FIGS. 1A and 1B taken along lines 2—2.

FIG. 2 is a cross-sectional view of the retainer shown in FIGS. 1A and 1B taken along line 2—2 of FIG. 1B, illustrating base 22 with molded passageway 26 extending from the base 22. Preferably, base 22 is approximately 3.350 inches (85.09 millimeters) by 1.375 inches (34.925 millimeters) in order to conform to commonly accepted overall dimensions of conventional suture packages and display boxes. The retainers are preferably about 0.010 inches (0.254 millimeters) thick.

Typical sizes and diameters of sutures from the standard United States Pharmacopeia (U.S. Pharmacopeia Convention, Inc., elsewhere abbreviated U.S.P.) are listed below.

| U.S.P. Size | U.S.P. Diameter. Inches. Max. |
| --- | --- |
| 7-0 | 0.002 |
| 6-0 | 0.004 |
| 5-0 | 0.006 |
| 4-0 | 0.008 |
| 3-0 | 0.010 |
| 2-0 | 0.013 |
| 1-0 | 0.016 |
| 1 | 0.019 |
| 2 | 0.022 |
| 3 | 0.025 |

While these sizes are most common, one skilled in the art would realize that other sizes can be used with the retainer of the present invention. In the embodiment of FIGS. 1-5, passageway 26 is substantially wider than conventional molded suture retainer passageways and should be at least times the diameter of the largest suture to be disposed therein. Preferably the passageway has a depth which is at least about twice the diameter of the largest suture to be placed therein and a width of at least about four times the diameter of the suture. This relatively wide passageway 26 permits the easy insertion, storage and removal of folded sutures without the creation of undesirable kinks and bends in the suture. Depending on the size of the base and the number of sutures to be retained, the passageway may be made wider and, if necessary, deeper. For example, width ranges of between about 0.10 and 0.30 inches and depth ranges of between about 0.05 and 0.07 inches are contemplated. For most common suture sizes a passageway of about 0.060 inches (1.524 millimeters) deep and 0.200 inches (5.080 millimeters) wide is preferred (see FIG. 2).

Figure 3A:
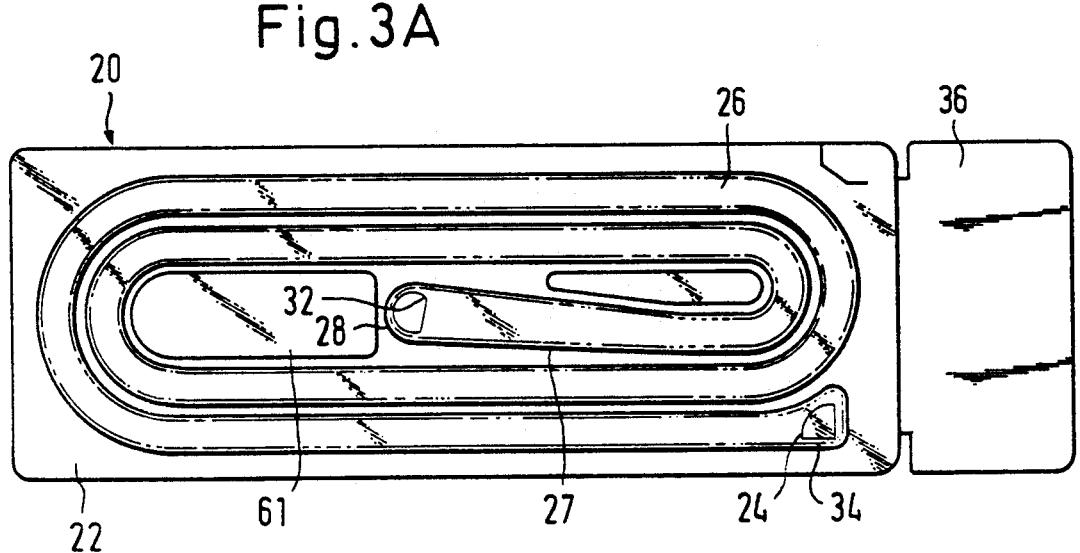
FIG. 3A is a bottom plan view of the molded suture retainer of FIGS. 1A and 1B.
Figure 3B:
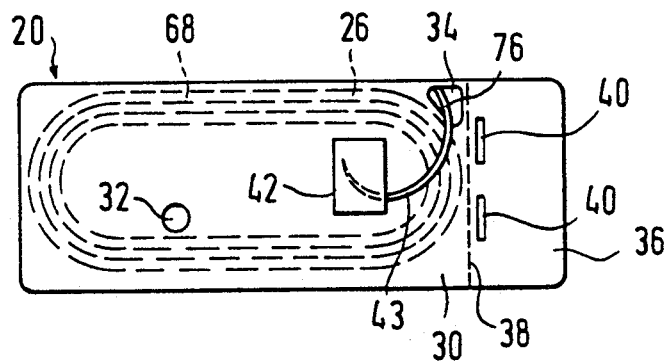
FIG. 3B is a top plan view of a molded suture retainer incorporating a needle park attached to the cover sheet.

Referring now to FIG. 3B, there is shown an appropriate cover sheet 30 for the retainer shown in FIGS. 1A and 1B. Cover sheet 30 is configured and dimensioned to overlie the open top of the retainer 20. In FIG. 3B, passageway 26 is shown in phantom to illustrate the relationship of the cover sheet to the molded retainer. The cover sheet is provided with a vacuum aperture 32 and a suture entrance aperture 34. Cover sheet 30 is adhesively attached to the molded retainer 20 and covers the passageway 26. In a preferred embodiment the cover sheet is adhered to the retainer with a hot melt adhesive, such as Oliver 18B adhesive coating available from Oliver Products of Minneapolis, Minn.

Vacuum aperture 32 aligns and communicates with the central vacuum receiving section 28 of the molded retainer 20. Similarly, suture entrance aperture 34 aligns and communicates with the suture receiving section 24. Preferably, cover sheet 20 is constructed of a material which is pervious to ethylene oxide sterilizing gas. The preferred material is a spun bonded polyolefin, such as Tyvek 1073B available from E.I. DuPont de Nemours & Co.

As shown in FIG. 3B, the preferred cover sheet 30 includes a fold-over panel 36 joined to the main section of the cover sheet at a perforated score line 38 with openings 40. Where armed sutures are to be loaded, a foam needle park 42, adhered to the outside of cover sheet 30, can be provided for holding a needle 43 in place during storage. See FIG. 1A. Retainer 20 is well suited for doubled over or doubled armed sutures and is preferred for tripled over sutures.

Figure 4:
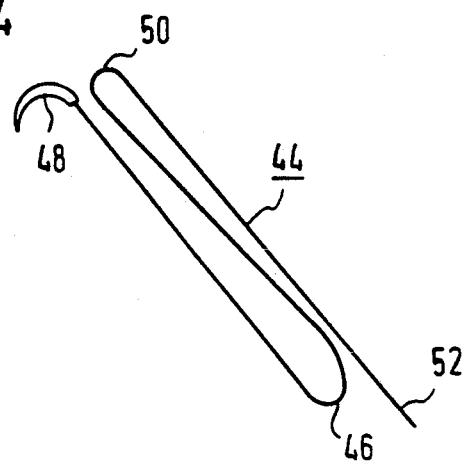
FIG. 4 is an illustration of a tripled-over suture.

Referring to FIG. 4, in order to load a tripled over suture into the retainer 20 of FIGS. 1A and 1B, a suture 44, such as a suture which is thirty six or more inches in length, is looped to form a first curved or half loop section 46 distal to the needle 48 and a second curved or half loop section 50 adjacent the needle. A suture tail end 52 extends beyond the first curved section 46. Preferably, tail end 52 extends beyond first curved loop section by a distance of at least about one inch.

Figure 5:
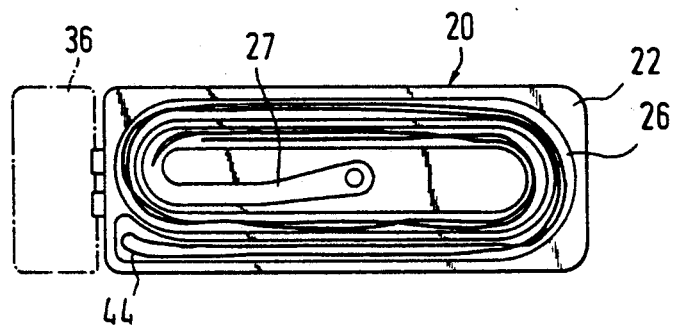
FIG. 5 is a plan view of a molded suture retainer showing a tripled over suture loaded therein.

With vacuum applied to the retainer, such as by placing a vacuum block (not shown) over vacuum aperture 32 (see FIG. 3B), suture tail end 52 and then first curved section 46 are sequentially inserted through suture entrance aperture 34 into passageway 26 while holding the suture adjacent the needle 48 and the second curved section 50. The suture is drawn into the retainer 20 by vacuum until the needle 48 is disposed adjacent suture aperture 34. In this embodiment, it is important that suture tail end 52 extend beyond the first curved section 46 at all times so that a knot is not inadvertently formed in the suture during insertion or removal from the retainer. FIG. 5 shows a bottom view of an unarmed tripled over suture 44 loaded within the wide passageway 26 of the molded suture retainer 20.

Figure 6:
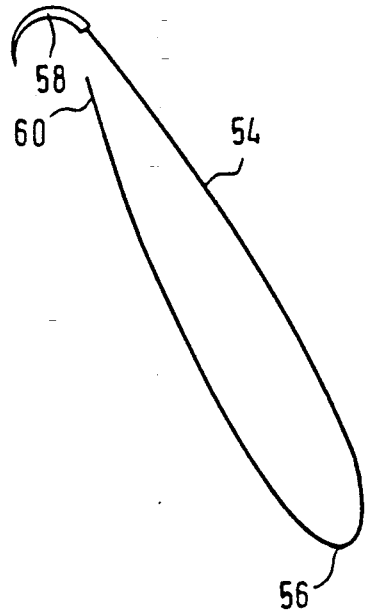
FIG. 6 is an illustration of a doubled-over suture.

For halved or doubled over sutures as shown in FIG. 6, the suture 54 is looped proximate its midpoint 56 to form two approximately equal lengths. Loading is accomplished in a manner similar to that described above with respect to the tripled over suture with the exception that no extended suture tail end need be formed. With vacuum applied, needle 58 and suture end 60 are grasped while inserting midpoint suture loop 56 through suture entrance aperture 34 into passageway 26. The suture 54 is drawn into the retainer 20 by vacuum until the needle is disposed adjacent the suture aperture 34.

Where sutures without needles are to be loaded into retainers, the above described loading procedures are equally applicable. Instead of inserting the suture until the needle is disposed adjacent the suture aperture, however, a short length of suture is maintained outside the suture aperture to facilitate easy removal. Similarly, for double armed sutures, i.e. sutures having needles on either end of the suture, the folding and loading procedure is the same as that described above for the halved suture 54 of FIG. 6, the only difference being the inclusion of a second needle at the suture end 60.

As an alternate insertion technique for double armed needles, it is contemplated that one needle could be disposed in the needle park prior to drawing the suture into the retainer under vacuum. That is, one needle would be placed in the needle park with the blunt end of the needle adjacent suture entrance aperture 34, then the suture would be drawn into the retainer under vacuum until the second needle is also adjacent the suture entrance aperture and can similarly be placed in the needle park.

Heretofore, embodiments of folded sutures have been described as being loaded singly with one suture per retainer. It is also envisaged that a plurality of these folded sutures can be loaded into and retained by a single molded suture retainer. In those cases, each of the sutures will be fed simultaneously through the suture entrance aperture 34 while a vacuum is applied to passageway 26 through vacuum aperture 32.

As stated, cover sheet 30 preferably includes a fold over panel 36. Fold over panel 36 covers the needle and suture during storage and is moved to an open position upon opening the outer package containing the suture and retainer. In the case of nonabsorbable sutures, the suture and retainer may simply be enclosed in a so-called "breather pouch" suitable for gas sterilization, such as a pouch consisting on one side of polyolefin (Tyvek) and a clear plastic on the other, such as polyethylene. The breather pouch is opened by peeling the two sides of the breather pouch apart and opening the fold over panel to reveal the needle or suture end, which may be grasped to remove the suture from the retainer by pulling.

Figure 7:
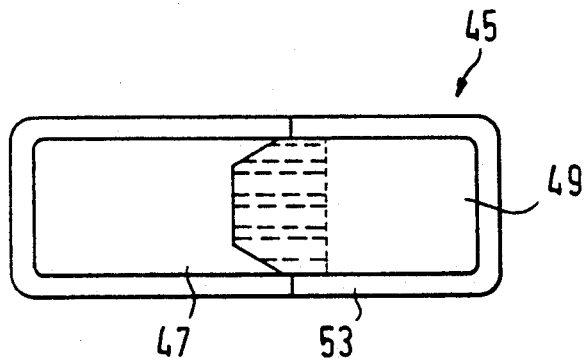
FIG. 7 is a plan view of a suture package in accordance with another embodiment of the invention.
Figure 8:
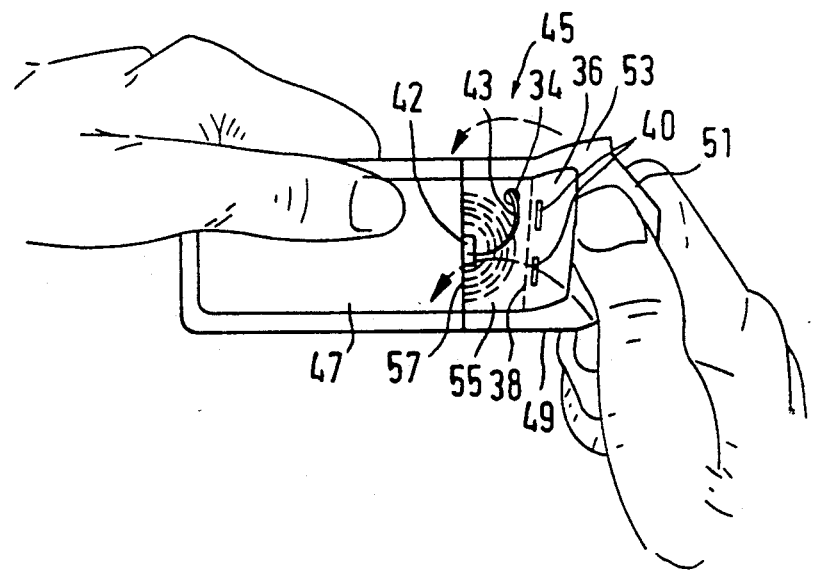
FIG. 8 is a plan view showing the opening procedure for a suture package in accordance with the embodiment of FIG. 7.
Figure 17:
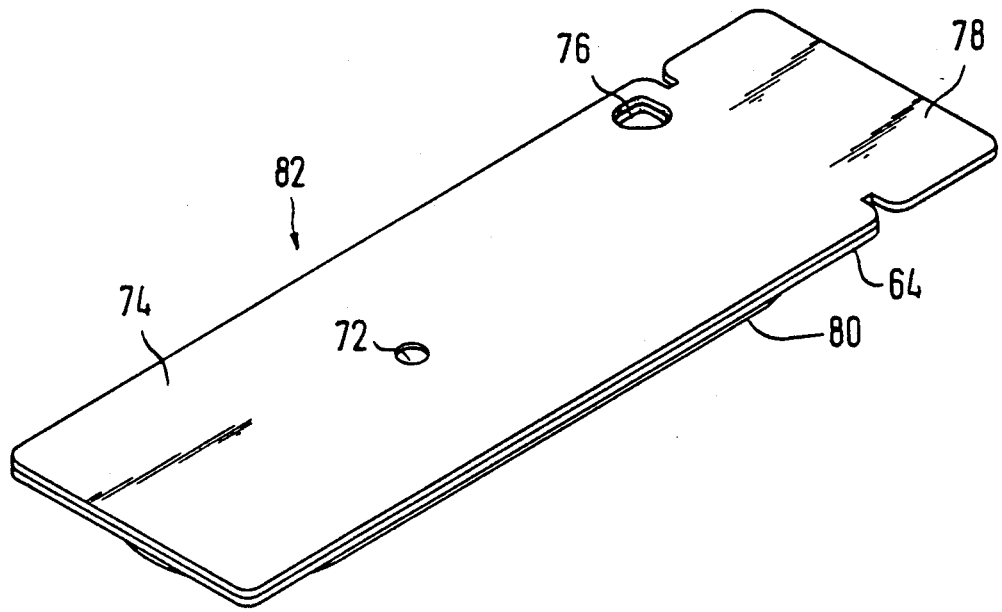
FIG. 17 is a perspective view of the top of a molded suture retainer in accordance with another embodiment of the present invention.
Figure 18:
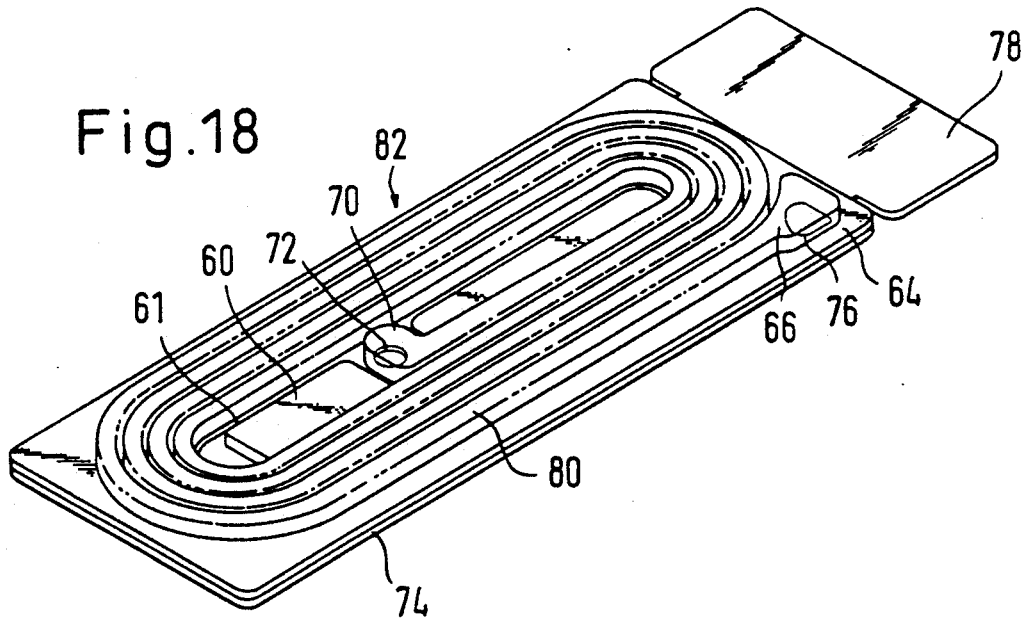
FIG. 18 is a perspective view of the bottom of a molded suture retainer in accordance with the embodiment of FIG. 17.

In the case of synthetic absorbable sutures, the retainer would be packaged in a foil laminate envelope which would be further packaged within an outer breather pouch. The preferred inner pouch is the peelable pouch as shown in FIGS. 7 and 8. FIG. 7 is a top plan view of the preferred peelable pouch in the closed position, and FIG. 8 illustrates the pouch partially peeled open. The peelable inner pouch 45 has a top layer comprised of first and second top panels 47, 49, respectively. The first and second top panels are adhered to each other substantially transversely, leaving a gripping tab 51. The top panels are adhered to a bottom panel 55 at a peripheral seal 53, i.e. at the transverse and longitudinal edges of the inner pouch or envelope, so as to define a pocket for receiving a suture retainer. As shown in FIG. 8, first top panel 47 does not extend the full length of bottom panel 55, but terminates at a first top panel transverse edge 57.

Upon peeling the inner pouch open, needle 43 is seen protruding from suture aperture 34 in the cover sheet and is held in position by needle park 42. The needle is plainly visible and accessible for removal of the suture from the passageway (shown in phantom) in the retainer. Preferably, fold over panel 36 is adhered to second top panel 49, so that upon opening the peelable inner pouch the needle is fully revealed and accessible. Top panels 47, 49 and bottom panel 55 may be constructed of a foil laminate material with a hot melt adhesive on the inner surface of each panel for forming peripheral seal 53 and the seal between the overlapping first and second top layer panels.

The foregoing peelable pouch is preferred, but it will be understood that other types of envelopes, such as conventional tearable foil laminate envelopes, can be used. See, for example, U.S. Pat. Nos. 3,939,969 and 4,014,433. It is contemplated that the suture could be sterilized by ethylene oxide permeating through an opening in the peelable pouch which is subsequently sealed, and that the peelable pouch itself should be sterilized and maintained sterile in an outer breather pouch in a known manner. See, for example, U.S. Pat. Nos. 3,815,315 and 4,603,538. Openings 40 facilitate ingress and egress of the sterilizing gas which enters through openings in the peelable pouch. Further, fold over panel 36 serves in part as a stand-off between the interior surface of the peelable pouch and the exterior of the Tyvek cover sheet 30 so as to allow better circulation of the sterilizing gas around the molded suture retainer.

The molded suture retainer in accordance with one embodiment of the present invention for absorbable sutures includes recess 61 for receiving a package stabilizing element 60 to keep the moisture content of the suture to within acceptable limits. Recess 61 may be accessible either from the top (FIG. 16) or from the bottom (FIG. 24) of the molded suture retainer 62. Where access is from the top, preferably the package stabilizing element 50 is put into place prior to covering the base 22 with the cover sheet 30. It is also envisaged to provide an access hole in the cover sheet to allow a package stabilizing element to be inserted therethrough after the cover sheet has been adhered to the base. Where access to recess 61 is from the bottom of the molded suture retainer 62, the package stabilizing element 60 is either set or adhered in place prior to final insertion of the retainer 62 into further packaging, for example, the peelable pouch 45. Walls 75 (FIG. 24) optionally may be provided to define recess 61. Alternatively, the package stabilizing element 60 may be dimensioned to fit within the confines of spiral passageway 80.

The recess 61 provides a correctly dimensioned space for the package stabilizing element 60 and is preferably centrally located on the molded suture retainer surrounded by passageway 26, although any location within the retainer is acceptable. The overall height of the recess and package stabilizing element retained therein preferably does not exceed the overall height of the molded suture retainer. Package stabilizing element 60 comprises a carrier element, such as a pad of paper or other cellulosic material, impregnated with a stabilizing agent composition.

Parent U.S. patent application Ser. No. 07/568,089, filed Aug. 16, 1990, the entire contents of which are incorporated herein by reference, discloses a stabilizing agent composition which comprises a storage stabilizing amount of a mixture of at least one water soluble hygroscopic polyhydroxy compound or ester thereof and a thickening compound. Many kinds of pharmaceutically acceptable non-aqueous thickeners can be utilized including water-soluble polysaccharides, e.g., hydroxypropyl methylcellulose (HPMC), and the other materials of this type which are disclosed in European Patent Application 0 267 015, polysaccharide gums such as guar, xanthan, and the like, gelatin, collagen, etc. An especially preferred class of thickeners are the saturated aliphatic hydroxycarboxylic acids of up to 6 carbon atoms and the alkali metal and alkaline earth metal salts and hydrates thereof. Within this preferred class of compounds are those of the general formula

wherein R is a hydrogen or methyl, R' is alkali metal or alkaline earth metal, and N is 0 or 1 and hydrates thereof.

Preferably, the components which make up the stabilizing agent composition have no appreciable toxicity for the body at the levels present. With these requirements in mind, those skilled in the art are readily capable of identifying any number of compounds which may be useful in the practice of this invention. Among the specific water-soluble hygroscopic polyhydroxy compounds or esters thereof which can be used herein with generally good results are glycerol and its mono- and diesters derived from low molecular weight carboxylic acids, e.g., monoacetin and diacetin (respectively, glyceryl monoacetate and glyceryl diacetate), ethylene glycol, diethylene glycol, triethylene glycol, 1,3-propanediol, trimethylolethane, trimethylolpropane, pentaerythritol, sorbitol, and the like. Glycerol is especially preferred. Mixtures of the afore-discussed polyhydroxy compounds or esters, e.g., sorbitol dissolved in glycerol, glycerol combined with monoacetin and/or diacetin, etc., are also useful. Compounds within the general formula (I) above, useful in formulating the stabilizing agent composition include, for example, salts of lactic acid such as calcium lactate, potassium lactate, sodium lactate, salts of glycolic acid, such as calcium glycolate, potassium glycolate, sodium glycolate, salts of 3-hydroxy propanoic acid, such as the calcium, potassium and sodium salts thereof, salts of 3-hydroxybutanoic acid, such as the calcium, potassium and sodium salts thereof and the like. As stated hereinbefore, hydrates of the compounds within the scope of the general formula (I) hereinabove are also within the scope of the present invention. Calcium lactate, especially calcium lactate pentahydrate, is a particularly preferred thickener.

If necessary or desirable, the stabilizing agent can be dissolved in any suitable non-aqueous solvent or combination of solvents prior to use. To be suitable, the solvent must (1) be miscible with the storage stabilizing agent at the concentration of the latter, (2) have a sufficiently high vapor pressure to be readily removed by evaporation, and (3) not appreciably affect the integrity of the polymeric article. Applying these criteria to a preferred storage stabilizing agent, glycerol and calcium lactate, lower alcohols such as methanol and ethanol are entirely suitable solvent carriers.

Generally, the stabilizing agent composition is comprised of a mixture of a compound within formula (I) hereinabove, such as calcium lactate, and a water soluble hygroscopic polyhydroxy compound, such as glycerol, in a weight ratio of between about 1:1 to about 1:10, most preferably 1:7, respectively. When a solvent, such as methanol, is utilized in the preparation of the stabilizing agent, the solvent is employed in amounts to provide a solution concentration of from about 20% to about 50%, preferably about 30% to about 45%, based on the total weight of the solution.

Most types of packaging, including the preferred inner peelable pouch, will allow some moisture passage through the laminate and the adhesive seal area of the pouch. The purpose of placing a carrier element impregnated with stabilizing agent, such as a paper sheet impregnated with a glycerine-containing composition, in the suture pouch is to maintain a consistent moisture level. The advantages of the package stabilizing element system of the present invention are described in greater detail in parent application Ser. No. 07/568,089, filed Aug. 16, 1990. Preferably, where recesses are provided in the molded suture retainer for retaining the package stabilizing element and the foam needle park, these recesses are configured to be substantially flush with the top edge of the retainer 20 or be contained within the height of the retainer. This allows for efficient storage of the retainers in stacked relation and will avoid the instability caused by projecting structure above the edge of the retainer when multiple retainers are stacked one upon the other.

In another embodiment of the present invention shown in FIGS. 9-16, a molded suture retainer 62 is provided for retaining at least one suture therein. As shown, retainer 62 has a base portion 64 and an enlarged suture receiving section 66 communicating with a spiraled passageway 68 spiraling toward the approximate central portion of retainer 62. Spiraled passageway 68 terminates at a unique vacuum receiving section 70 which is angularly offset from the terminus of the spiral passageway. This angular offset communicates with the vacuum aperture 72 in cover sheet 74 and serves to prevent the end of the suture from being drawn out of vacuum aperture 72 where it would be exposed to damage, entanglement, etc.

Cover sheet 74 is configured and dimensioned to overlie the open top of retainer 62 and to be adhesively attached thereto in a manner as described above with respect to the first embodiment thereof. In addition to the vacuum aperture 72, cover sheet 74 has a suture entrance aperture 76 in alignment with suture receiving section 66 and a needle park aperture 77 for accessing the recessed needle park 79 from the top of the retainer. This configuration allows needles to be at least partially inserted into needle park 79 from the top of the retainer through needle park aperture 77. As in previous embodiments, cover sheet 74 is constructed of a material impervious to bacteria while still being pervious to ethylene oxide sterilizing gas.

Cover sheet 74 may include a fold-over panel 78 joined to the main section of the cover sheet to facilitate removal thereof and to cover and protect the suture entrance aperture 76 and the needle park aperture 77 and needles therein. This fold-over panel 78 also serves to prevent the needles form contacting and possibly puncturing the packaging material.

FIGS. 17-24 show a variation of the molded suture retainer of FIGS. 9-16 configured to retain a longer suture therein. The added length is accommodated by extending the spiral passageway 80. Other elements of the retainer 82 are substantially the same as those described above with respect to the molded suture retainer of FIGS. 9-16.

Figure 25:
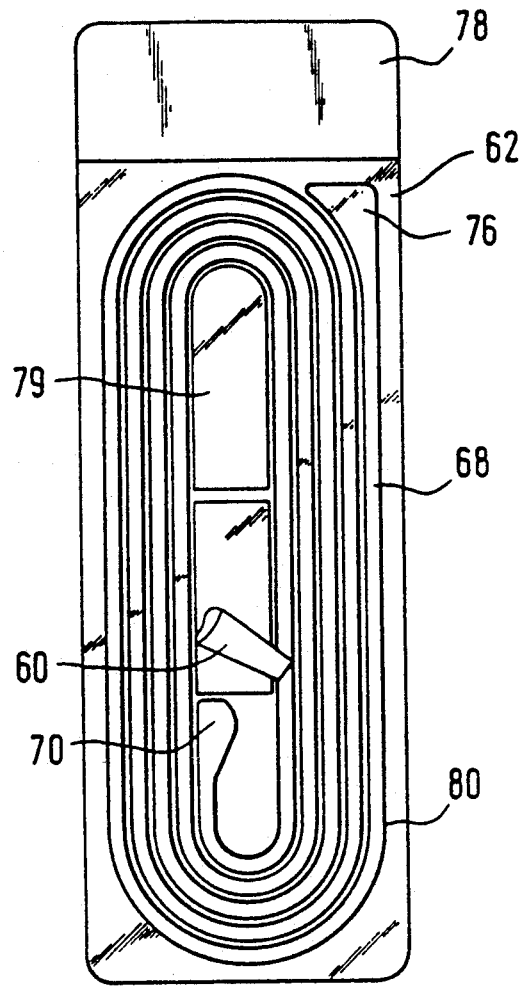
FIG. 25 is a bottom plan view of an embodiment of the present invention showing the package stabilizing element in place.
Figure 26:
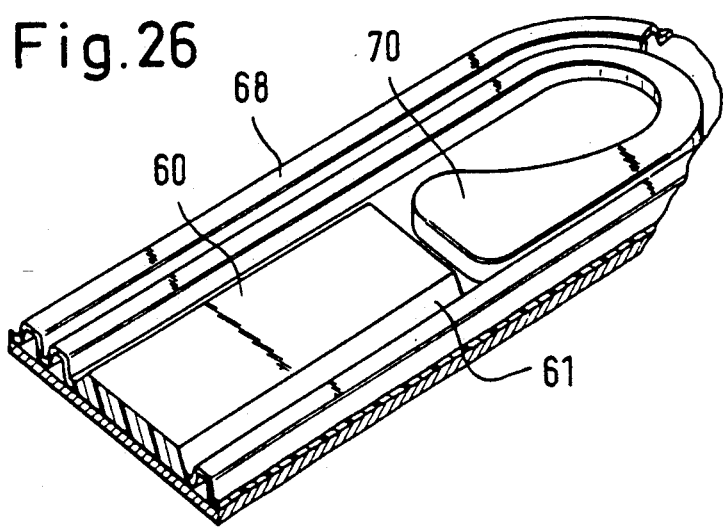
FIG. 26 is a perspective view in partial cross section of the embodiment of FIG. 25.

FIGS. 25 and 26 show a preferred embodiment of the present invention incorporating both a recess for receiving a package stabilizing element 61 and a recessed needle park 79 in substantially the same horizontal plane as the spiral passageway 80. This configuration demonstrates the maximum efficient use of spacing in the retainer without the need to extend the height of the retainer.

To the extent not already indicated, it also will be understood by those of ordinary skill in the art that any one of the various specific embodiments herein described and illustrated may be further modified to incorporate features shown in other of the specific embodiments.

The invention in its broader aspects therefore is not limited to the specific embodiments herein shown and described but departures may be made therefrom within the scope of the accompanying claims without departing from the principles of the invention and without sacrificing its chief advantages.

What is claimed is:

1. A suture retainer for packaging sutures comprising:
   a molded cover member having a substantially spiral passageway formed therein, said passageway defining a channel, open at the top and interconnecting a suture receiving section at a proximal end thereof with a vacuum receiving section at a distal end thereof, said vacuum receiving section being angularly offset from said distal end of the channel;
   a recess formed in said molded cover member for receiving a needle park therein; and
   a cover sheet adhered to said molded cover member to close said channel, said cover sheet including a suture entrance aperture aligned with said suture receiving section, a vacuum aperture aligned with said vacuum receiving section and a needle park aperture aligned with said recess.

2. A suture retainer as in claim 1 further comprising a recess for receiving a package stabilizing element.

3. A suture retainer as in claim 1 wherein said molded cover member is formed from a moldable plastic material.

4. A suture retainer as in claim 1 wherein said cover sheet is constructed of a material which is pervious to ethylene oxide sterilizing gas.

5. A suture retainer as in claim 1 wherein said spiraled passageway is configured in an oval pattern spiraling toward the approximate center of said molded member.

6. A molded suture retainer as in claim 1 further comprising a peelable pouch having:
   a) an outer envelope of substantially moisture impervious material characterized by longitudinal side edges and top and bottom transverse edges, the envelope including first and second walls adhered to each other along their edges to define an accessible pocket between them for receiving said suture retainer; and
   b) a peelable closure flap hingedly adhered to an outer peripheral portion of said first and second walls and sealing access to the pocket of the outer envelope, the closure flap terminating in a grip-facilitating tab whose free edge terminates a distance away from the bottom transverse edges of the outer envelope.

7. A suture retainer as in claim 2 wherein said recess for receiving a package stabilizing element is dimensioned to retain a package stabilizing element substantially flush with said cover sheet.

8. A suture retainer as in claim 2 wherein said recess for receiving a package stabilizing element is dimensioned to receive and retain a package stabilizing element without increasing the thickness of the molded cover member and cover sheet.

9. A suture retainer as in claim 8 further comprising a package stabilizing element disposed in said recess.

10. A suture retainer as in claim 1 wherein said recess for receiving a needle park therein is dimensioned to retain a needle park substantially flush with said cover sheet.

11. A molded suture retainer as in claim 10 further comprising a needle park disposed in said recess.

12. A molded suture retainer as in claim 1 further comprising a recess for receiving a package stabilizing agent therein.

13. A suture retainer as in claim 3 wherein said molded plastic material is substantially transparent.

14. A suture retainer as in claim 11 wherein said package stabilizing element comprises a carrier element impregnated with a stabilizing agent composition comprising a polyhydroxy compound or ester thereof and at least one compound having the general formula

wherein R is a hydrogen or methyl, R' is a metal selected from the group consisting of alkali metal and alkaline earth and n is 0 or 1, and hydrates thereof.

15. A suture retainer as in claim 14 wherein the carrier element comprises a paper pad.

16. A suture retainer as in claim 14 wherein said stabilizing agent composition comprises a mixture of glycerol and calcium lactate.

17. The molded suture as in claim 12 wherein said recess for receiving a needle park and said recess for receiving a package stabilizing agent are disposed within the confines of the spiral passageway.

18. A molded suture retainer as in claim 17 wherein said recesses are configured to retain respectively, a needle park and a package stabilizing agent substantially flush with said cover sheet.

19. A molded suture retainer as in claim 17 wherein said recesses for receiving a package stabilizing element and a needle park are dimensioned to receive and retain a package stabilizing element and a needle park respectively without increasing the thickness of the molded cover member and cover sheet.

20. A suture retainer for packaging sutures comprising:
   a molded cover member having a substantially spiral passageway formed therein, said passageway defining a channel, open at the top and interconnecting a suture receiving section at a proximal end thereof with a vacuum receiving section at a distal end thereof;
   a cover sheet adhered to said molded cover member to close said channel, said cover sheet including a suture entrance aperture aligned with said suture receiving section and a vacuum aperture aligned with said vacuum receiving section; and
   a needle park adhered to said cover sheet.

21. A suture retainer as in claim 20 wherein said cover sheet further comprises a fold-over panel joined to said cover sheet and dimensioned to cover said suture entrance aperture.

22. A suture retainer as in claim 20 further comprising a recess, disposed in said molded cover member, for receiving a package stabilizing agent.

23. A suture retainer as in claim 22 wherein said recess for receiving a package stabilizing agent is formed within the confines of the spiral passageway.

24. A suture retainer as in claim 22 wherein said recess for receiving a package stabilizing element is dimensioned to receive and retain a package stabilizing element without increasing the thickness of the molded cover member and cover sheet.

25. A suture retainer as in claim 22 further comprising a package stabilizing element disposed in said recess.

26. A suture retainer for packaging sutures comprising:
- a molded cover member having a substantially spiral passageway formed therein, said passageway defining a channel, open at the top and interconnecting a suture receiving section at a proximal end thereof with a vacuum receiving section at a distal end thereof;
- a cover sheet adhered to said molded cover member to close said channel, said cover sheet including a suture entrance aperture aligned with said suture receiving section, and a vacuum aperture aligned with said vacuum receiving section, and a needle park aperture;
- a first recess, formed in said molded cover member, for receiving a package stabilizing element therein, and a second recess, aligned with said needle park aperture, for receiving a needle park therein.

27. A suture retainer as in claim 26 wherein said vacuum receiving section is angularly offset from the distal end of the channel.

28. A suture retainer as in claim 26 wherein said first recess for receiving a package stabilizing agent is formed within the confines of the spiral passageway.

29. A suture retainer as in claim 26 wherein said first recess for receiving a package stabilizing element is dimensioned to receive and retain a package stabilizing element without increasing the thickness of the molded cover member and cover sheet.

30. A molded suture retainer as in claim 26 further comprising a package stabilizing element disposed in said first recess for receiving a package stabilizing element.

31. A suture retainer as in claim 26 wherein said recess for receiving a needle park is formed within the confines of the spiral passageway.

32. A suture retainer as in claim 26 wherein said recess for receiving a needle park is dimensioned to receive and retain a needle park without increasing the thickness of the molded cover member rand cover sheet.

33. A suture retainer as in claim 26 further comprising a needle park disposed in said recess for receiving a needle park.

* * * * *

UNITED STATES PATENT AND TRADEMARK OFFICE
CERTIFICATE OF CORRECTION

PATENT NO. : 5,246,104

DATED : September 21, 1993

INVENTOR(S) : Brown et al.

It is certified that error appears in the above-identified patent and that said Letters Patent is hereby corrected as shown below:

Col. 1, line 41, "3,8766,068" should read --3,876,068--

Signed and Sealed this

Twelfth Day of April, 1994

Attest:

BRUCE LEHMAN

Attesting Officer    Commissioner of Patents and Trademarks